(12) United States Patent
Tellenbach

(10) Patent No.: US 12,722,005 B2
(45) Date of Patent: Sep. 1, 2026

(54) STIMULATION PATTERN ENCODING AND TRANSFER PROTOCOL FOR TENS AND NMES DEVICES

(71) Applicant: NMES Group AB, Svenljunga (SE)

(72) Inventor: Vincent Tellenbach, Sion Valais (CH)

(73) Assignee: NMES Group AB, Svenljunga (SE)

( * ) Notice: Subject to any disclaimer, the term of this patent is extended or adjusted under 35 U.S.C. 154(b) by 310 days.

(21) Appl. No.: 18/030,479

(22) PCT Filed: Oct. 6, 2021

(86) PCT No.: PCT/EP2021/077616
§ 371 (c)(1),
(2) Date: Apr. 5, 2023

(87) PCT Pub. No.: WO2022/074077
PCT Pub. Date: Apr. 14, 2022

(65) Prior Publication Data

US 2023/0372711 A1 Nov. 23, 2023

Related U.S. Application Data

(60) Provisional application No. 63/198,239, filed on Oct. 6, 2020.

(51) Int. Cl.
*A61N 1/36* (2006.01)
*A61N 1/04* (2006.01)

(52) U.S. Cl.
CPC ....... *A61N 1/36034* (2017.08); *A61N 1/0456* (2013.01); *A61N 1/36031* (2017.08)

(58) Field of Classification Search
CPC ........................ A61N 1/36034; A61N 1/36031
USPC ........................................................... 607/59
See application file for complete search history.

(56) References Cited

U.S. PATENT DOCUMENTS

2012/0310306 A1* 12/2012 Klostermann ..... A61N 1/37252 607/60
2015/0073500 A1 3/2015 Kothandaraman et al.
2018/0043158 A1 2/2018 Thakur et al.

FOREIGN PATENT DOCUMENTS

EP 1 174 163 A1 1/2002

OTHER PUBLICATIONS

International Search Report dated Jan. 28, 2022, in connection with International Application No. PCT/EP2021/077616.
European Examination Report dated Apr. 24, 2026, in connection with European Application No. 21794317.4.

* cited by examiner

*Primary Examiner* — Nadia A Mahmood
(74) *Attorney, Agent, or Firm* — Wolf, Greenfield & Sacks, P.C.

(57) ABSTRACT

A method for encoding electrical stimulation sequence or program and transferring them to an electrical stimulation device for the treatment of medical and non-medical conditions. NeuroMuscular Electrical Stimulation (NMES) and Transcutaneous Electrical Nerve Stimulation (TENS) consists of delivering short electrical impulses to the user. These impulses are characterized by their shape, polarity, amplitude, duration and impulse-to-impulse duration. This encoding method focuses on the impulse amplitude, polarity, duration and impulse-to-impulse duration. The stimulation program can be adjusted in real time using data transmitted by various sensors.

17 Claims, 11 Drawing Sheets

Figure 5
Figure 6
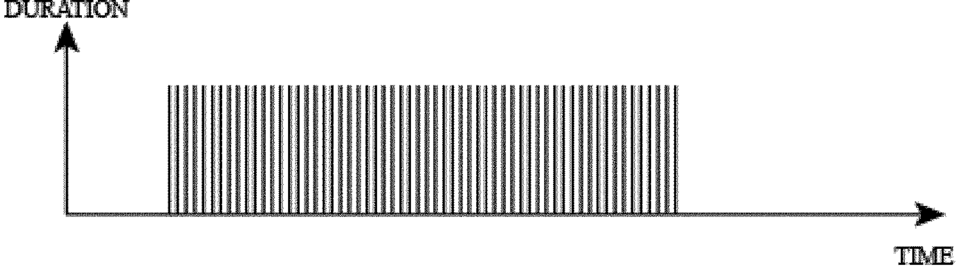
Figure 7
| 0–7 | 8–15 | 16–23 | 24–31 | 32–47 bit |
| --- | --- | --- | --- | --- |
| RAMP OPCODE | IMPULSE FREQUENCY | IMPULSE START DURATION | IMPULSE STOP DURATION | NUMBER OF IMPULSES TO GENERATE |
Figure 8

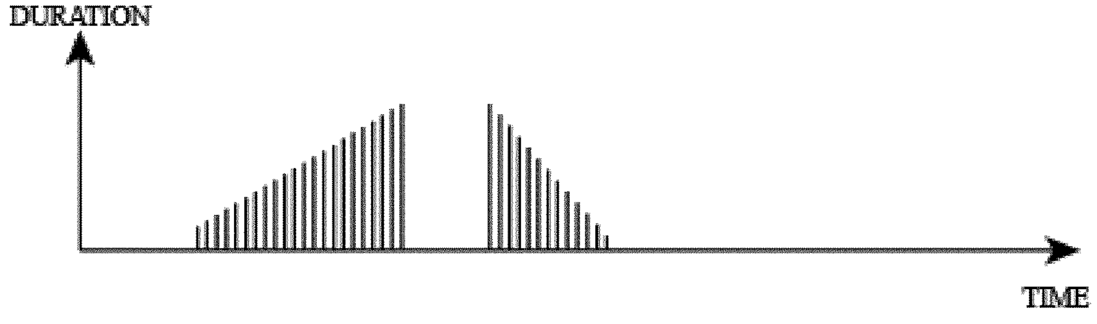
Figure 9
| 0 – 7 | 8 – 23 | 24 – 31 bit |
|---|---|---|
| DURATION-FREQUENCY MODULATION OPCODE | RELATIVE ADDRESS OF ARRAY OF IMPULSE VALUES | REPEAT PATTERN |
Figure 10
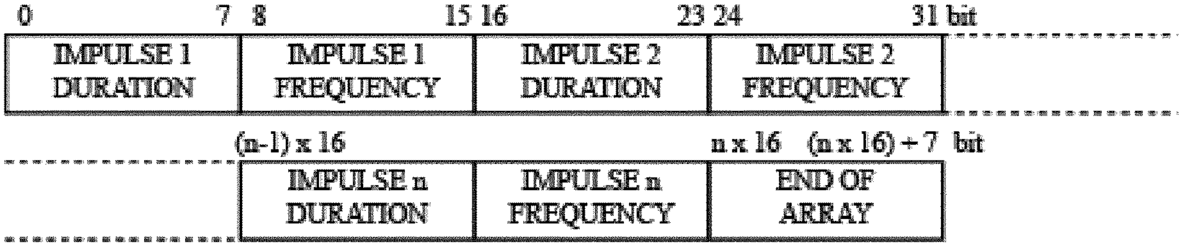
Figure 11

| 0 – 7 | 8 – 23 | 24 – 31 | 32 – 39 bit |
|---|---|---|---|
| DURATION-MODULATION OPCODE | RELATIVE ADDRESS OF ARRAY OF IMPULSE VALUES | IMPULSE FREQUENCY | REPEAT PATTERN |

| 0 – 7 | 8 – 15 | 16 – 23 | 24 – 31 bit | |
|---|---|---|---|---|
| IMPULSE 1 DURATION | IMPULSE 2 DURATION | IMPULSE 3 DURATION | IMPULSE 4 DURATION | ... |

| | | (n-1) x 8 | n x 8 – (n x 8) + 7 bit |
|---|---|---|---|
| ... | IMPULSE n-1 DURATION | IMPULSE n DURATION | END OF ARRAY |

| 0 … 7 | 8 … 23 | 24 … 31 | 32 … 39 bit |
|---|---|---|---|
| FREQUENCY-MODULATION OPCODE | RELATIVE ADDRESS OF ARRAY OF IMPULSE VALUES | IMPULSE DURATION | REPEAT PATTERN |

| 0 … 7 | 8 … 15 | 16 … 23 | 24 … 31 bit |
|---|---|---|---|
| IMPULSE 1 FREQUENCY | IMPULSE 2 FREQUENCY | IMPULSE 3 FREQUENCY | IMPULSE 4 FREQUENCY |

| | (n-1) x 8 | n x 8 | (n x 8) + 7 bit |
|---|---|---|---|
| IMPULSE n-1 FREQUENCY | IMPULSE n FREQUENCY | END OF ARRAY | |

STIMULATION PATTERN ENCODING AND TRANSFER PROTOCOL FOR TENS AND NMES DEVICES

CROSS REFERENCE TO RELATED APPLICATIONS

This Application is a national stage filing under 35 U.S.C. § 371 of International Patent Application Serial No. PCT/EP2021/077616, filed on Oct. 6, 2021, entitled STIMULATION PATTERN ENCODING AND TRANSFER PROTOCOL FOR TENS AND NMES DEVICE, which claims the benefit of U.S. Provisional Application No. 63/198,239, filed on Oct. 6, 2020. The contents of these applications are incorporated herein by reference in their entirety.

FIELD OF THE INVENTION

The present invention relates, in general, to the encoding of electrical stimulation patterns for electrical stimulation impulses, methods of adapting said patterns, and systems for performing the methods.

BACKGROUND

The number of medical applications that use electrical stimulation is large and covers virtually every living body component. These applications include prevention of muscle atrophy, promotion of wound healing, prevention of venous thrombosis, alleviation of both chronic/acute pain and prevention of incontinence to name but a few. Electrical stimulation may also be used for such non-medical objectives as muscle training, muscle toning, improving muscle endurance, and muscle relaxation.

Electrical stimulation of muscles and nerves is well established in medicine and physical therapy with a history dating back to mid-1850; such stimulation is currently achieved by applying electrodes to: 1) the skin at the point(s) of desired electrical stimulation; 2) through insertion of electrical probes into body cavities, and; 3) through surgical insertion of electrodes.

Neuromuscular Electrical Stimulation Principle

Muscle contractions are produced and controlled by the brain by means of electrical signals transmitted through the nervous system. When an electrical signal from the brain reaches the muscle, the latter is activated into groups of "motor units", each made up of a single neuron and of a group of associated muscle cells connected to it. This initiates a chemical reaction which causes the cells in this motor unit to contract. The complete contraction of the muscle usually involves a number of motor units simultaneously, and its strength is directly proportional to the number of activated motor units. The gradual enrolment process of the motor units which consents to a perfectly controlled and smooth muscle contraction is called spatial summation.

Electrical muscle stimulation (EMS), also known as neuromuscular electrical stimulation (NMES) or electromyostimulation, is the elicitation of muscle contraction using electric impulses. The impulses are generated by a device and are delivered through electrodes on the skin near to the muscles being stimulated. The electrodes are generally pads that adhere to the skin. The impulses mimic the action potential that comes from the central nervous system, causing the muscles to contract.

When a sufficiently intense single electrical impulse reaches the motor muscle or nerve, it causes one short single contraction of the muscle (spasm). If this single spasm is repeated and the frequency of reiteration exceeds ten spasms p.s., each following spasm is enhanced by one degree of muscle shortening caused by the preceding spasm. Such an effect is called temporal summation. The lowest stimulation frequency, where the successive contractions merge, is called tetanization frequency.

Neither the design of the electrical impulses for clinical efficacy, nor the methods by which the data defining the impulses reaches a conductive medium for application to the skin have been considered or developed in the known art.

There is no prior art associated with the use of stimulation pattern encoding and real time adjustment of such patterns to improve the effects of the electrical stimulation using the user's response to the electrical stimulus.

SUMMARY

The invention is defined by the appended independent claims. Embodiments of the invention are defined in the dependent claims.

In a first aspect of the invention, there is provided a method for providing an encoded stimulation pattern to a device for providing electrical stimulation impulses to a user, the method comprising: generating a header section, the header section comprising program metadata; generating a body section, the body section comprising an impulse stimulation program; generating a footer section, the footer section comprising error detection data; concatenating the header section, body section, and footer section, to form an encoded stimulation pattern; and transmitting the encoded stimulation pattern to the device.

An encoded stimulation pattern of this form is advantageous for a number of reasons.

Safety and Efficacy for the User

An encoded stimulation pattern according to the invention is advantageous because it guarantees safety for the user, due to the error detection data. The error detection data provides data in the transmitted pattern that allows the receiving device to verify that the exact intended pattern has been sent and received. Not only does this ensure that a clinically effective stimulation pattern is affected, but it also ensures that the pattern is safe to use. If certain opcodes or parameters were corrupted during transmission, the stimulation device could attempt to affect an unsafe stimulation pattern, for example with too great an amplitude. The particular form of the encoded stimulation patter of the present invention negates this risk. In certain embodiments, the stimulation device performs an error checking step, verifying that the stimulation pattern received is correct, using the error detection data, before proceeding to implement the stimulation pattern.

Efficiency and Power Requirements

An encoded stimulation pattern according to the present invention also provides all of the information required to produce a stimulation pattern in a data string. A user of the device is thus not required to input large numbers of parameters and/or operating modes via a user interface, thereby allowing the potential to save space on the device, and the possibility to reduce power consumption on the device in order to set up a stimulation program. A reduction in power requirements is advantageous to reduce the heat and noise generated by the device. Furthermore, if the device incorporates a portable power supply, for example a battery, the power supply may be made smaller while maintaining similar device run time and/or the run time may be increased for a certain size of power supply.

Transmitting, as used herein, may refer to local transmission between components, for example between hardware components physically connected to one another, or remote transmission by a wireless protocol, for example Bluetooth Low Energy.

The program metadata may comprise at least one of: a pattern ID number; a pattern name; a number of phases; a maximal intensity; and a pattern duration. The error detection data may comprise a checksum. The pattern metadata may allow the stimulation device to identify the pattern to be run, for example if it has received this pattern before and stored it in a cache, the stimulation device may check the received pattern against the stored pattern as an additional check that the data has been received without error.

The impulse stimulation program may comprise an operational code and at least one parameter related to the operational code.

The operational code may be selected from: contraction; ramp; duration-frequency-modulation; duration-modulation; frequency-modulation; loop; back; phase; polarity; impulse-duration-multiply; and finish.

The at least one parameter may be selected from: impulse frequency; impulse duration; number of impulses to generate; impulse start duration; impulse stop duration; relative address of array of impulse values; repeat program; end of array; repeat loop; phase number; intensity change percentage; phase duration; polarity value; and impulse duration multiply value.

In this way, encoded stimulation patterns according to the invention have a broad range of applicability to the needs of the user, and can be effective and safe while fulfilling any clinical and/or non-clinical need the user has.

The body section may comprise a plurality of impulse stimulation programs. Impulse stimulation programs may also be referred to herein as commands.

In a second aspect of the invention, there is provided a method for providing an adaptable encoded stimulation pattern to a device for providing electrical stimulation impulses to a user, the method comprising: generating an encoded stimulation pattern; transmitting the encoded stimulation pattern to the device; receiving data from the device relating to a measured parameter of the user; modifying the encoded stimulation pattern in response to the received data; and transmitting the modified stimulation pattern to the device.

In this way, the provision of stimulation impulses to a user can be adaptive, and maintain safety and efficacy, by being instructed by a measured biometric characteristic of the user. For example, if a motion sensor detects that no movement has been affected in a muscle during a program intended to cause muscle contractions, the stimulation pattern may be modified to increase amplitude, impulse length impulse frequency, or any other parameter as will be clear to a person skilled in the art. Equally, if the motion sensor detects user distress due to excess movement, the power of the stimulation pattern can be reduced by reducing one of the same parameters. The feedback provided by the user instructs more effective and safe provision of stimulation impulses. Modifying the encoded stimulation impulse may include ceasing its operation entirely.

The measured parameter of the user may comprise at least one of: motion; heart rate; skin temperature; and skin bioimpedance. These characteristics of users have been found to be particularly efficient to measure and particularly instructive in providing information as to how the stimulation pattern is being received by a user. In some embodiments, stimulation devices according to the present invention comprise at least one of: a motion sensor; a temperature sensor; a heart rate sensor; and a skin bioimpedance sensor.

The encoded stimulation pattern may comprise: a header section, the header section comprising program metadata; a body section, the body section comprising an impulse stimulation program; and a footer section, the footer section comprising error detection data. An encoded stimulation pattern having this form has been found to be particularly advantageous for reasons given above.

The impulse stimulation program may comprise an operational code and at least one parameter related to the operational code, and wherein modifying the encoded stimulation pattern in response to the received data comprises at least one of: changing the operational code; and increasing or decreasing at least one parameter. It has been found that modifying these components of the stimulation program is an effective way to control the efficacy and safety of the provided stimulation patterns.

The device for providing electrical stimulation impulses to a user may be in communication with a mobile device, and wherein generating the encoded stimulation pattern and/or modifying the encoded stimulation pattern is performed on a processor on the mobile device. In this way, the more complex processing required to generate, transmit, and in some cases, modify, encoded stimulation patterns is removed from the stimulation device. This is advantageous because it removes the need for the stimulation device to have a user interface, and vastly reduces the size and power requirements of the stimulation device. A reduction in power requirements is advantageous as described above.

Reducing the size of the device is advantageous because it is beneficial for devices suitable for providing electrical stimulation to muscles and/or nerves to be as small as possible. Some forms of such devices may need to be worn during exercise, such that both weight and physical size are important parameters, and even those worn while the user is stationary may be advantageously reduced in size to aid portability and ease of use.

The device for providing electrical stimulation impulses to a user may communicate with the mobile device via a wireless communication protocol, optionally wherein the wireless communication protocol is Bluetooth Low Energy. It has been found that Bluetooth Low Energy is particularly suited to this purpose, since the stimulation device and mobile device will often be in close proximity to one another, thus a low energy wireless communication protocol is sufficient, and has reduced size and power constraints versus other wireless communication protocols.

The encoded stimulation pattern may be configured to affect a non-medical and/or non-therapeutic effect in the user.

The encoded stimulation pattern and/or modified encoded stimulation pattern may be transmitted to the device suitable to provide stimulation impulses to a user in multiple data packets. This may be advantageous because the stimulation device may start to process, and, in some cases where safety allows, begin to apply stimulation impulses to the user, before the entirety of the encoded stimulation pattern has been sent. The efficiency of the method can thus be increased. Furthermore, in embodiments in which modification of the stimulation pattern takes place, this is simplified if the data packets in need of modification have not yet been sent to the stimulation device. These packets can be modified before transmission, instead of requiring an additional transmission, thereby reducing the total data sent between the devices; there are clear efficiency and power advantages associated with operation in this manner.

In a third aspect of the invention, there is provided a data processing apparatus comprising means for carrying out the steps of methods according to the invention.

In a fourth aspect of the invention, there is provided a computer program, comprising instructions which, when the pattern is executed by a computer, cause the computer pattern to carry out the steps of methods according to the invention.

In a fifth aspect of the invention, there is provided a computer readable storage medium having stored thereon the computer program according to the fourth aspect.

In a sixth aspect of the invention, there is provided a device for providing electrical stimulation impulses to a user, comprising a data processing apparatus according to the third aspect or a computer readable storage medium according to the fifth aspect.

In a seventh aspect of the invention, there is provided a system, comprising: a mobile device comprising: a data processing apparatus according to the third aspect and/or a computer readable storage medium according to the fifth aspect; and a device for providing stimulation impulses to a user, wherein the mobile device and the device for providing electrical stimulation impulses to a user are configured to communicate with one another via a wireless communication protocol.

The methods as described herein enable the encoding of the stimulation pattern in an efficient fashion in order to optimize the memory use of the stimulation device processor, provide a fast and secure transfer of data and finally offer the possibility to adjust the stimulation parameters in real time according to the user or patient response to the electrical stimulus.

The methods as described herein may be computer-implemented methods. As will be described in greater detail throughout, the methods may be performed on a processor at the stimulation device, in local communication with the stimulation device, or in wireless communication with the stimulation device.

It is an object of the present invention to provide a method for encoding the stimulation pattern. It is an object of the present invention to provide an alternative to the current practice of storing the complete set of stimulation patterns in the stimulation device processor memory or a dedicated memory chip. It is an object of the present invention to use the encoding of the stimulation pattern in order to optimize the memory use of the stimulation device. It is an object of the present invention to provide a method allowing the real time adjustment of the impulse parameters using data from physiological sensors monitoring the user movements or response to the electrical stimulus.

It is an object of the present invention to provide electric stimulation delivery that overcomes shortcomings in prior art devices. A further object of the present invention is to provide an electric stimulation method, using encoding and transferring of stimulation pattern, that delivers electrical impulses that trigger strong, effective muscle contractions or nerve responses in a stimulated object (individual). Another object of the present invention is to provide an electric stimulation device that may be safely operated by medical and non-medical users. A further object of the present invention is to provide electric stimulation that is simple and safe to use. A still further object of the present invention is to provide electric stimulation that is cost and size effective for both professionals and users.

The foregoing and other objects and advantages will appear from the descriptions that follow. In the description reference is made to the accompanying drawings, which forms a part hereof, and in which is shown by way of illustration specific principles of the control method in which the invention may be practiced. These principles will be described in sufficient detail to enable those skilled in the art to practice the invention, and it is to be understood that other principles may be utilized and that structural changes may be made without departing from the scope of the invention, for example, modifications in algorithms.

BRIEF DESCRIPTION OF THE DRAWINGS

FIG. 5 depicts the structure of a command for use with embodiments of the invention.

FIG. 6 depicts a contraction command for use with embodiments of the invention.

FIG. 7 depicts a pattern of electrical impulses generated by the contraction command.

FIG. 8 depicts a ramp command for use with embodiments of the invention.

FIG. 9 depicts a pattern of electrical impulses generated by the ramp command.

FIG. 10 depicts a duration-frequency-modulation command for use with embodiments of the invention.

FIG. 11 depicts the structure of an array containing the duration and frequency values for each impulse of a duration-frequency-modulation command.

DETAILED DESCRIPTION

Figure 1:
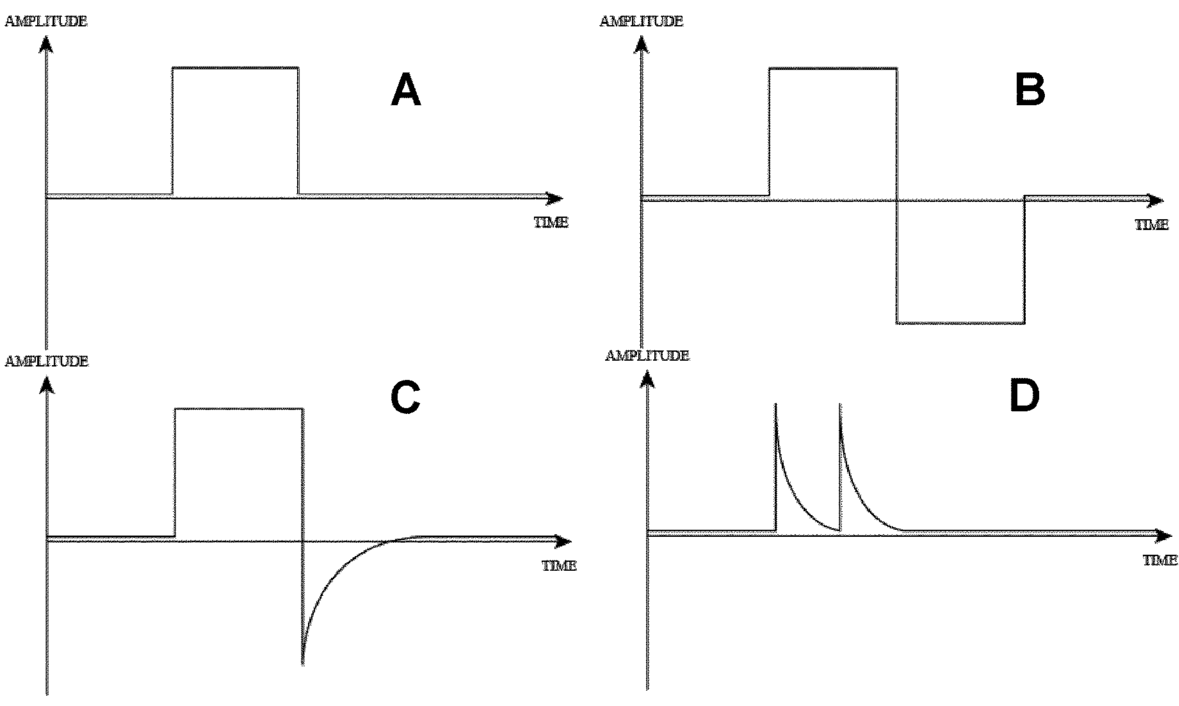
FIG. 1A depicts a monophasic impulse.
FIG. 1B depicts a biphasic symmetric impulse.
FIG. 1C depicts a biphasic asymmetric impulse.
FIG. 1D depicts a high voltage impulse.

FIG. 1 shows four exemplary waveforms, A to D. Waveform A illustrates the waveform of a monophasic impulse. The impulse consists of a unique phase which can be either on the positive or negative amplitude. Waveform B illustrates the waveform of a biphasic symmetric impulse. The impulse consists of two phases which can start either on the positive or negative amplitude. The second phase has the same shape as the first phase but on the opposite polarity. Waveform C illustrates the waveform of a biphasic asymmetric impulse. The impulse consists of two phases which can start either on the positive or negative amplitude. The second phase has a different shape as the first phase and on the opposite polarity. Waveform D illustrates the waveform of a high voltage impulse. The impulse consists of one or multiple spikes of amplitude with a very short duration.

NMES Impulse Parameters

The adjustable electrical parameters in TENS include pulse intensity or amplitude, frequency or inter-pulse-interval IPI, duration and waveform.

Impulse Intensity/Amplitude

Figure 2:
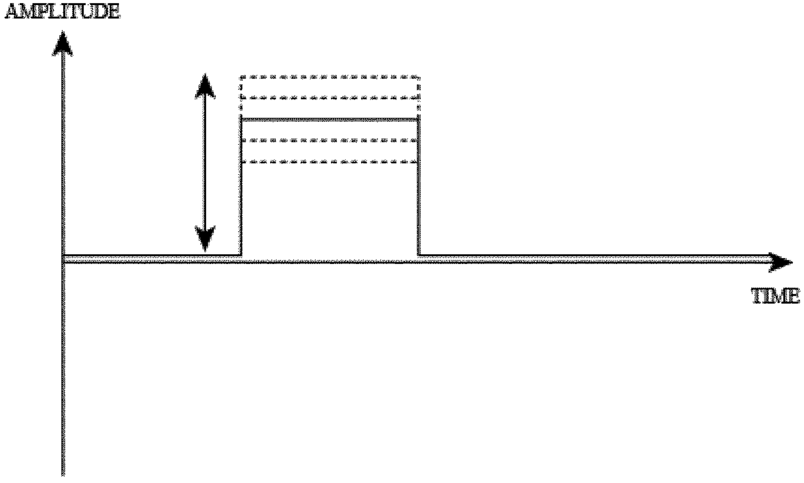
FIG. 2 depicts a intensity/amplitude parameter on a monophasic impulse.

Pulse intensity is broadly classified as three levels depending on the response of the patient; sensory, motor, microcurrent level. Sensory level intensity is defined as the amplitude making the patient feels a comfortable paresthesia like tingling or tapping sensation without any motor contraction. This amplitude is also referred to low intensity, which is usually used for conventional TENS. Motor level intensity is defined as the amplitude producing a motor contraction with paresthesia. Sometime the intensity can be increased to the maximal level just before becoming noxious. Such an intensity is usually applied in intense NMES and TENS. Herein, the intensity is given as a percentage from 0 to 100. FIG. 2 illustrate the intensity/amplitude parameter on a monophasic impulse.

Impulse Frequency/Inter-Pulse-Interval IPI

Figure 3:
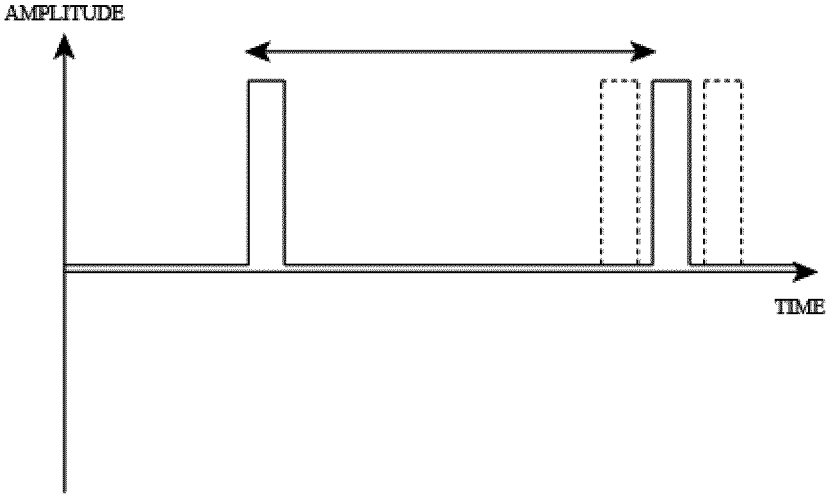
FIG. 3 depicts a frequency/IPI parameter.

Impulse frequency or inter-pulse-interval (IPI) of electrical current is usually classified as high frequency (>50 Hz), low frequency (<10 Hz) and burst (bursts of high frequency current applied at a much lower frequency). Different impulse frequencies will produce different effects on the stimulated nerves and muscles. In certain embodiments of the present invention, a maximum frequency value may be set at 240 Hz. FIG. 3 illustrates the frequency or IPI parameter.

Impulse Duration

Figure 4:
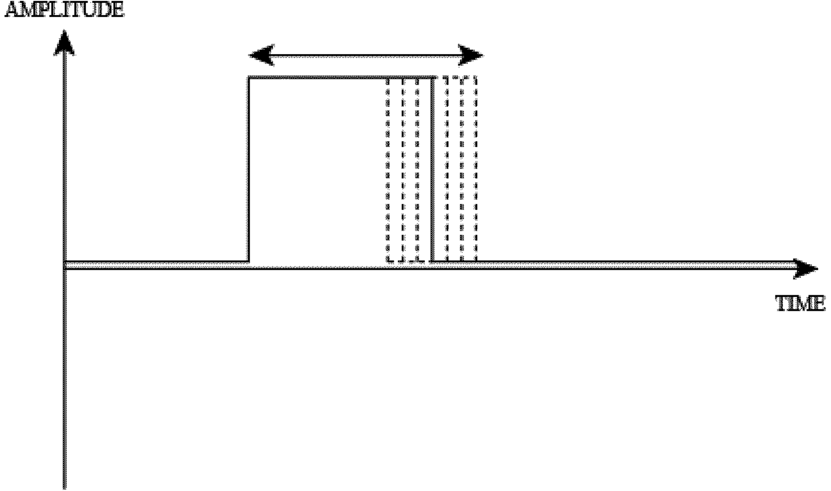
FIG. 4 depicts an impulse duration parameter.

Impulse duration is usually classified as longer (>200 microseconds) and shorter duration (<200 microseconds). It has been found that longer pulse duration evokes more intense sensation and a deeper effect than a shorter duration. In certain embodiments of the present invention, the maximal impulse duration is 500 microseconds. FIG. 4 illustrates the impulse duration parameter.

Encoding of Stimulation Patterns

It a first aspect of the present invention, there is provided a method allowing for the encoding of different stimulation patterns. These stimulation patterns are then affixed to each other to constitute a complete stimulation program. The stimulation program being processed by the NMES device main processor in order to generate electrical impulses. The pattern encoding consists of a set of commands in the form of an array of numeric values. These values can be in the unsigned byte format (8 bits from 0 to 255) or unsigned word format (16 bits from 0 to 65535). FIG. 5 shows the structure of a command. A command may also be referred to herein as a stimulation program, where a stimulation pattern additionally comprises a header and a footer. The first value corresponds to the opcode of the command. The opcode is always in the byte format. The data following the opcode are the different parameters attached to the opcode. The number of parameters varies from one opcode to another. The parameters are in byte format or word format.

The set of commands is divided into two categories:

1. Opcodes that generate impulses
2. Opcodes that do not generate impulses

Set of Commands that Generate Impulses

There are 5 commands that generate impulses, each described below.

1. Contraction

This command generates a given number of electrical impulses with the same duration and frequency. The intensity parameter set by the NMES device operator is not affected by this command. The contraction command has 3 parameters and has a total length of 40 bits. As shown in FIG. 6, the Contraction command consists of:

Contraction opcode (format: byte, bit 0 . . . 7)

Impulse frequency parameter (format: byte, bit 8 . . . 15, step: 1 Hertz)

Impulse duration parameter (format: byte, bit 16 . . . 23, step: 2 microseconds)

Number of impulses to generate (format: word, bit 24 . . . 39, step: 1 impulse)

FIG. 7 illustrates a pattern of electrical impulses generated by the Contraction command.

2. Ramp

This command generates a given number of electrical impulses with the same frequency and a duration varying from a start given value up to or down to a stop given value. If the stop value is greater than the start value, the impulse duration increases by a fixed step at each impulse. If the stop value is lower than the start value, the impulse duration decreases by a fixed step at each impulse. The increase or decrease step is calculated by the formula:

$$\text{step} = \frac{\text{Impulse Duration Stop Value} - \text{Impulse Duration Start Value}}{\text{Number of Impulses to Generate}}$$

The intensity parameter set by the NMES device operator is not affected by this command. The Ramp command has 4 parameters and has a total length of 48 bits. As shown in FIG. 8, the Ramp command consists of:

Ramp opcode (format: byte, bit 0 . . . 7)

Impulse frequency parameter (format: byte, bit 8 . . . 15, step: 1 Hertz)

Impulse start duration parameter (format: byte, bit 16 . . . 23, step: 2 microseconds)

Impulse stop duration parameter (format: byte, bit 24 . . . 31, step: 2 microseconds)

Number of impulses to generate (format: word, bit 32 . . . 47, step: 1 impulse)

FIG. 9 illustrates two patterns of electrical impulses generated by the Ramp command.

3. Duration-Frequency-Modulation

This command generates a given number of electrical impulses each having a specific frequency and duration. The frequency and duration of each impulse are stored in a separated array of values. The relative address at which this array is stored in the processor memory is used as one of the command parameters. The intensity parameter set by the NMES device operator is not affected by this command. The Duration-Frequency-Modulation command has 2 parameters and has a total length of 32 bits. As shown in FIG. 10, the Duration-Frequency-Modulation command consists of:

- Duration-Frequency-Modulation opcode (format: byte, bit 0 . . . 7)
- Relative address of impulses array parameter (format: word, bit 8 . . . 23, step: 1 byte)
- Number of times the pattern must be repeated parameter (format: byte, bit 24 . . . 31, step: 1)

FIG. 11 illustrates the structure of the array containing the duration and frequency values for each impulse. The array contains duration values in byte format and frequency value in byte format for each impulse. The last value of the array contains a tag indicating that no more impulse must be generated.

Figures 12, 13, 14:
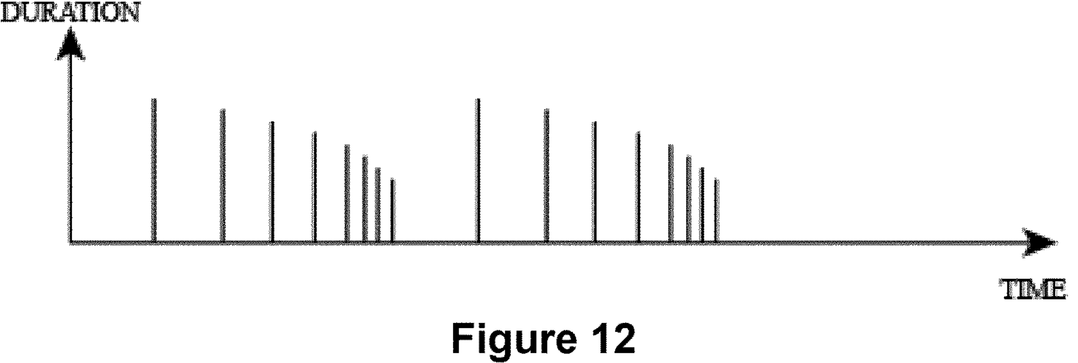
FIG. 12 depicts two patterns of electrical impulses generated by the Duration-Frequency-Modulation command.
FIG. 13 depicts a duration-modulation command for use with embodiments of the invention.
FIG. 14 depicts the structure of an array containing the duration values for each impulse of a duration-modulation command.

FIG. 12 illustrates two patterns of electrical impulses generated by the Duration-Frequency-Modulation command.

4. Duration-Modulation

This command generates a given number of electrical impulses with the same frequency each having a specific duration. The duration of each impulse is stored in a separated array of values. The relative address at which this array is stored in the processor memory is used as one of the command parameters. The intensity parameter set by the NMES device operator is not affected by this command. The Duration-Modulation command has 3 parameters and has a total length of 40 bits. As shown in FIG. 13, the Duration-Modulation command consists of:

- Duration-Modulation opcode (format: byte, bit 0 . . . 7)
- Relative address of impulses array parameter (format: word, bit 8 . . . 23, step: 1 byte)
- Impulse frequency parameter (format: byte, bit 24 . . . 31, step: 1 Hertz)
- Number of times the pattern must be repeated parameter (format: byte, bit 32 . . . 39, step: 1)

FIG. 14 illustrates the structure of the array containing the duration values for each impulse in byte format. The last value of the array contains a tag indicating that no more impulse must be generated.

Figures 15, 16, 17:
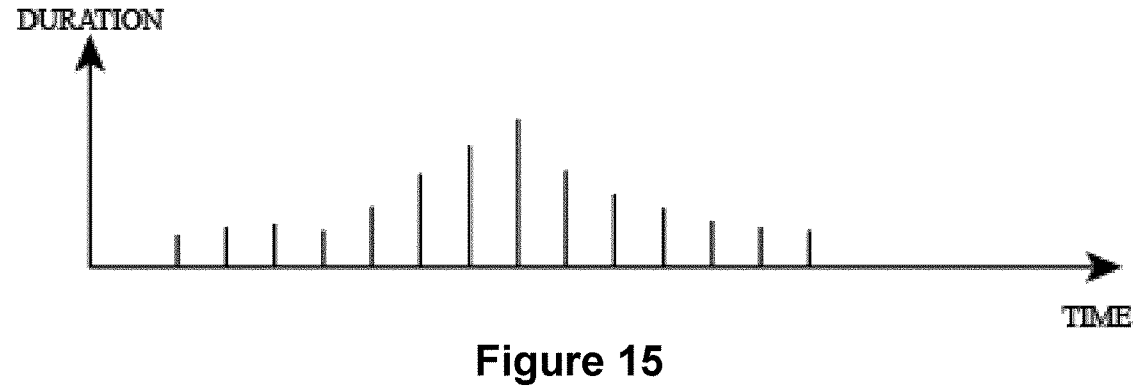
FIG. 15 depicts a pattern of electrical impulses generated by the duration-modulation command.
FIG. 16 depicts a frequency-modulation command for use with embodiments of the invention.
FIG. 17 depicts the structure of an array containing the frequency values for each impulse of a frequency-modulation command.

FIG. 15 illustrates a pattern of electrical impulses generated by the Duration-Modulation command.

5. Frequency-Modulation

This command generates a given number of electrical impulses with the same duration each having a specific frequency. The frequency of each impulse is stored in a separated array of values. The relative address at which this array is stored in the processor memory is used as one of the command parameters. The intensity parameter set by the NMES device operator is not affected by this command. The Frequency-Modulation command has 3 parameters and has a total length of 40 bits. As shown in FIG. 16, the Frequency-Modulation command consists of:

- Frequency-Modulation opcode (format: byte, bit 0 . . . 7)
- Relative address of impulses array parameter (format: word, bit 8 . . . 23, step: 1 byte)
- Impulse duration parameter (format: byte, bit 24 . . . 31, step: 1 Hertz)
- Number of times the pattern must be repeated parameter (format: byte, bit 32 . . . 39, step: 1)

FIG. 17 illustrates the structure of the array containing the frequency values for each impulse in byte format. The last value of the array contains a tag indicating that no more impulse must be generated.

Figure 18:
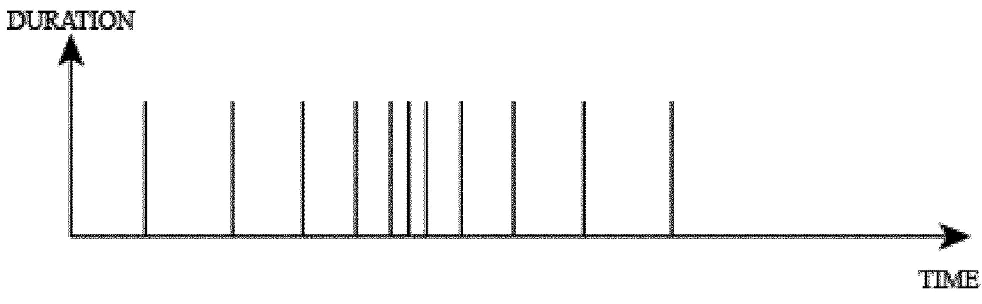
FIG. 18 depicts two patterns of electrical impulses generated by the frequency-modulation command.

FIG. 18 illustrates two patterns of electrical impulses generated by the Frequency-Modulation command.

Set of Commands that do not Generate Impulses

There are 6 commands that do not generate impulses

1. Loop

Figure 19:
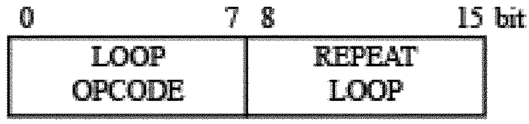
FIG. 19 depicts a loop command for use with embodiments of the present invention.

The Loop command allows the repetition of a pattern or a sequence of patterns for a given number of times. The Loop command must always be associated with the Back command. The Loop command has one parameter and has a total length of 16 bits. As shown in FIG. 19, the Loop command consists of:

- Loop opcode (format: byte, bit 0 . . . 7)
- Number of times the Loop must be repeated parameter (format: byte, bit 8 . . . 15, step: 1)

2. Back

Figure 20:
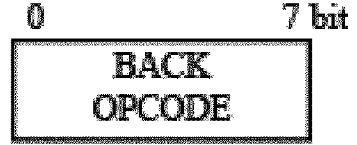
FIG. 20 depicts a back command for use with embodiments of the present invention.

The Back command is always associated with the Loop command and indicates the end of the pattern or sequence of patterns to be repeated. The Back command has no parameter and has a total length of 8 bits. As shown in FIG. 20, the Back command consists of:

- Back opcode (format: byte, bit 0 . . . 7)

3. Phase

Figure 21:
FIG. 21 depicts a phase command for use with embodiments of the present invention.

A stimulation program can be divided in different phases. The Phase command indicates the start of a new phase of the stimulation program. The Phase command has 3 parameters and has a total length of 40 bits. As shown in FIG. 21, the Phase command consists of:

- Phase opcode (format: byte, bit 0 . . . 7)
- Phase number parameter (format: byte, bit 8 . . . 15, step: 1)
- Phase intensity change in percent (format: byte, bit 16 . . . 23, step: 1%)
- Phase duration parameter (format: word, bit 24 . . . 39, step: 1 second)

4. Polarity

Figure 22:
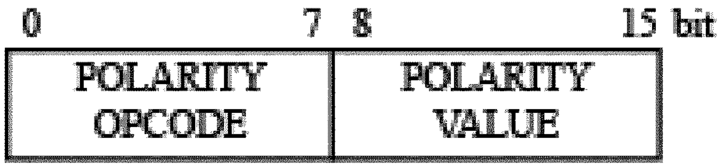
FIG. 22 depicts a polarity command for use with embodiments of the present invention.

The Polarity command allows for the selection of the impulse polarity. The Polarity command has one parameter and has a total length of 16 bits. As shown in FIG. 22, the Polarity command consists of:

- Polarity opcode (format: byte, bit 0 . . . 7)
- Polarity value parameter (format: byte, bit 8 . . . 15, step: 1)

The Polarity value parameter can have one of the following values:

| | |
|---|---|
| 0 | Impulse polarity is randomly selected. It could be either positive or negative. |
| 1 | Impulse polarity is positive |
| 2 | Impulse polarity is negative |
| 3 | Impulse polarity is alternated at each impulse |
| 4 | Impulse polarity is alternated at each Back command |

5. Impulse-Duration-Multiply

Figure 23:
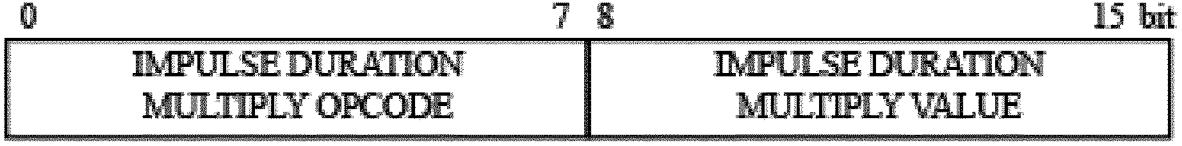
FIG. 23 depicts an impulse duration multiply command for use with embodiments of the present invention.

The Impulse-Duration-Multiply command allows for the multiplication of the impulse duration in order to generate longer electrical impulses. The Impulse-Duration-Multiply command has one parameter and has a total length of 16 bits. As shown in FIG. 23, the Impulse-Duration-Multiply command consists of:

Impulse-Duration-Multiply opcode (format: byte, bit 0 . . . 7)

Multiplication factor parameter (format: byte, bit 8 . . . 15, step: 1)

6. Finish

Figure 24:
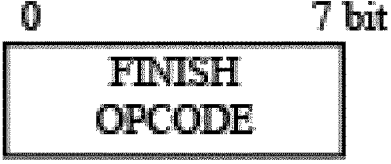
FIG. 24 depicts a finish command for use with embodiments of the present invention.

The Finish command indicates the end of the stimulation program. The Finish command has no parameter and has a total length of 8 bits. As shown in FIG. 24, the Finish command consists of:

Finish opcode (format: byte, bit 0 . . . 7)

Transfer of Stimulation Program

It is the subject of the present invention to provide a second method allowing the transfer of a stimulation program consisting of different patterns described above. The transfer is set to take place between a mobile application and a NMES device with Bluetooth Low Energy (BLE) capability. It is possible with this method, and others described herein, to create new stimulation programs or to adapt existing stimulation program based on feedback provided by sensors such as motion sensors, heart rate sensors, temperature sensors or skin bioimpedance sensors.

The feedback received from these sensors may be used to modify at least one of the opcode and the parameters used by the opcode.

For example, if any one of the sensors identifies that the user is in distress, for example increased heart rate and temperature beyond a first predefined threshold, the opcode may be modified from the next in the pattern (for example, Ramp), to become an opcode that does not generate an impulse (for example, Finish). The stimulation pattern will then cease.

Alternatively, if the heart rate and temperature are above a second predefined threshold, but below the first predefined threshold, the opcode may not be changed, but the associated parameter may be changed. Continuing the example with the "Ramp" opcode, a modification to the "number of impulses to generate" parameter may be used to reduce the number of impulses to generate, thereby reducing the total electrical stimulation applied to the user and the total time for which stimulation is applied.

It will be appreciated that the above examples using "ramp", "finish", and "number of impulses to generate" are exemplary only. Embodiments of the present invention may modify any opcode to another opcode, for example an impulse generating opcode to a non-impulse generating opcode, a non-impulse generating opcode to an impulse generating opcode, or changing between respective impulse generating or non-impulse generating opcodes (for example "ramp" to "contraction", or "phase" to "polarity"). Certain changes in opcode will necessitate an associated change in parameters, some will not. Embodiments of the present invention may also modify any parameter to another parameter and/or modify the magnitude of the parameter, as is technically feasible given which parameters are required as inputs by the opcodes currently being used.

Furthermore, measurements from any sensor described herein may be used to affect modifications to any opcode and/or parameter. No one sensor is linked to a modification of a specific opcode and/or parameter.

Stimulation Program Structure

Figure 25:
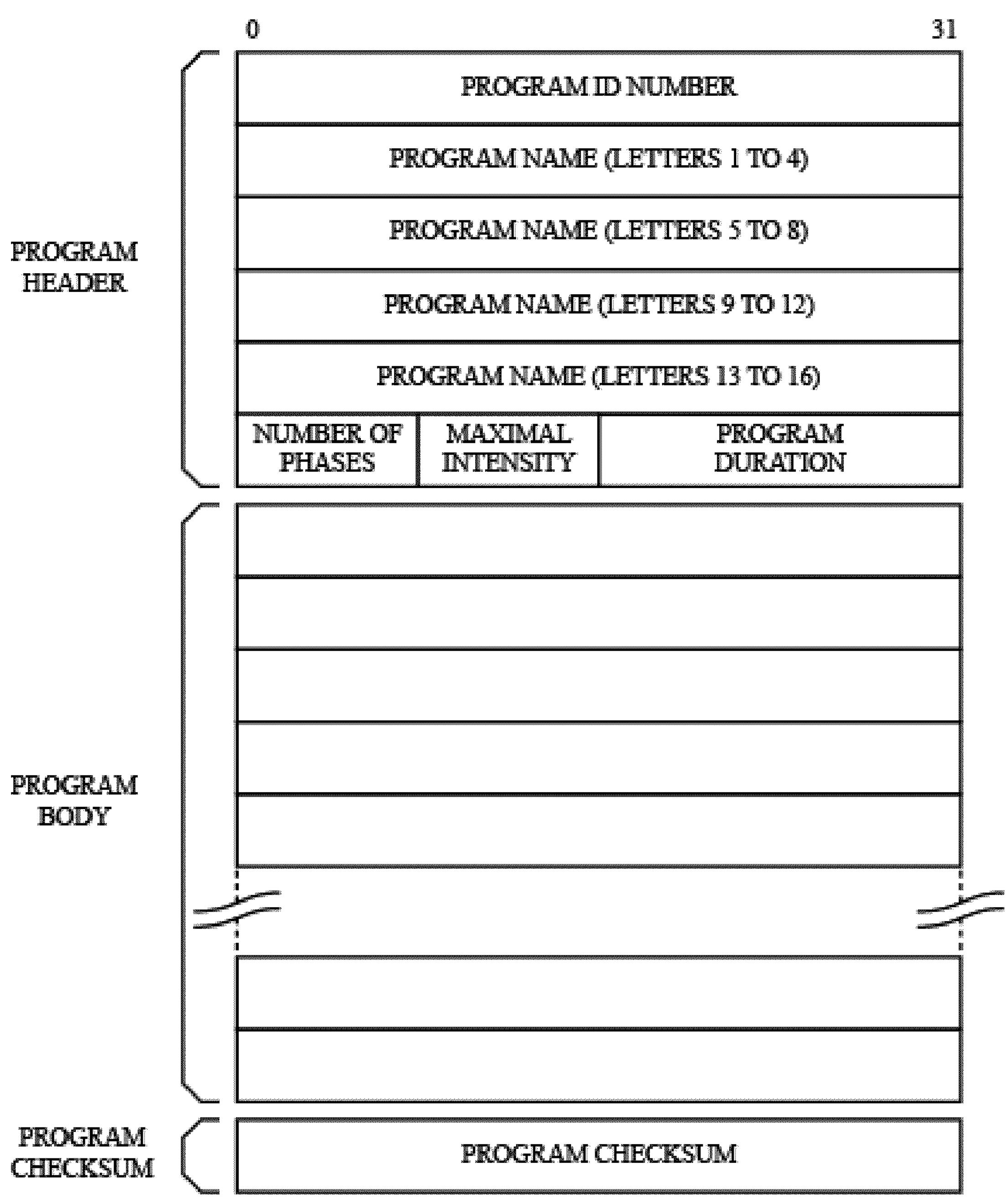
FIG. 25 depicts the structure of an encoded stimulation program according to an embodiment of the present invention.

The stimulation program structure is made of long word data of 32 bits each. FIG. 25 shows the structure of a stimulation program.

The stimulation program structure consists of three sections:

Header Section

The Header Section contains general information related to the stimulation program. The Header Section has a fixed length of 6 long words of 32 bits.

The first long word data contains the stimulation program ID number. The following four long word data contains the name of the stimulation program with a fixed length of 16 characters.

Each character is in a byte ASCII format of 8 bits. The sixth long word data contains the stimulation program number of phases coded on a byte of 8 bits, the maximal allowed intensity coded on a byte of 8 bits and the total duration of the stimulation program in seconds coded on a word data of 16 bits.

Body Section

The Body Section contains the stimulation patterns defined by the different commands described in method #1. The length of the Body Section is variable and depends on the commands used to build the stimulation program. In case the data constituting the Body Section do not fill completely the last long word data, the unused bits of this long word data are filled with a zero value.

Checksum Section

The Checksum Section contains the program checksum value which provides a simple way to verify the successful transfer of the full stimulation program structure from the mobile application to the NMES device. The checksum value is computed by adding all the long word data contained in the Header and Body sections truncated to the least significant 32 bits. When the NMES device process the stimulation program transfer, it will compute the checksum on its own end. At the end of the transfer, the checksum value computed by the NMES device is compared to the checksum provided at the end of the stimulation program structure. If both checksums are similar, the transfer was successfully processed.

Stimulation Program Transfer

The stimulation program is transferred from the mobile application to the NMES device by packets of one long word data of 32 bits. The mobile waits for an acknowledge message from the NMES device before sending the next data packet. The last long word data to be transferred is the program checksum. If this checksum matches the checksum computed by the NMES device the transfer is successful.

FIG. 25 shows the transfer process from the mobile application side.

Example Stimulation Patterns

Figure 26:
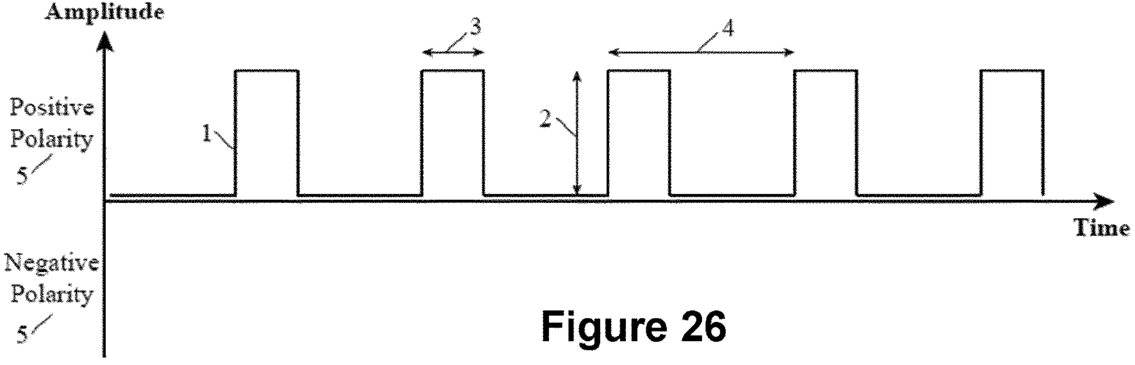
FIG. 26 depicts an exemplary stimulation pattern having consistent polarity.

FIG. 26 shows a stimulation pattern where all the electrical impulses (1) have the same specification in terms of amplitude (2), duration (3), impulse-to-impulse duration (4) and polarity (5).

Figure 27:
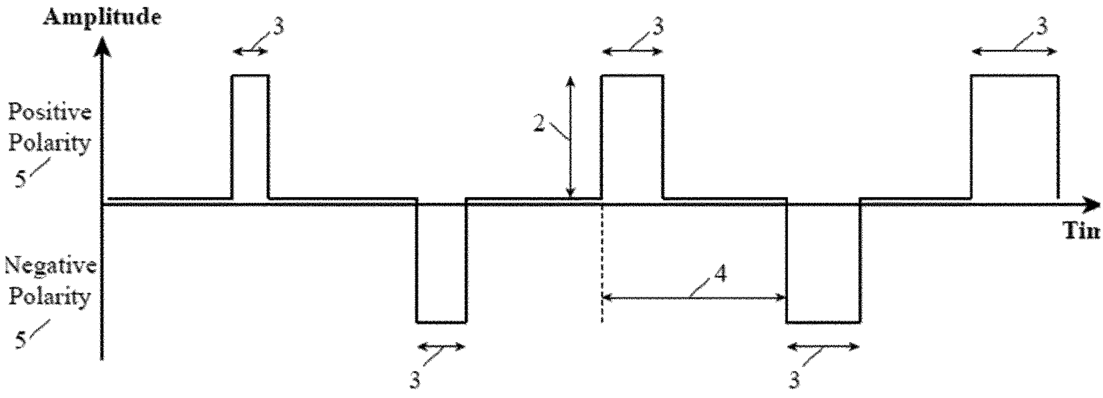
FIG. 27 depicts an exemplary stimulation pattern having inconsistent polarity.

FIG. 27 shows a stimulation pattern where the polarity (5) of impulses changes at each impulse and where the impulse duration (3) increases at each impulse. The impulse amplitude (2) and impulse-to-impulse duration (4) are constant for every impulse.

Figure 28:
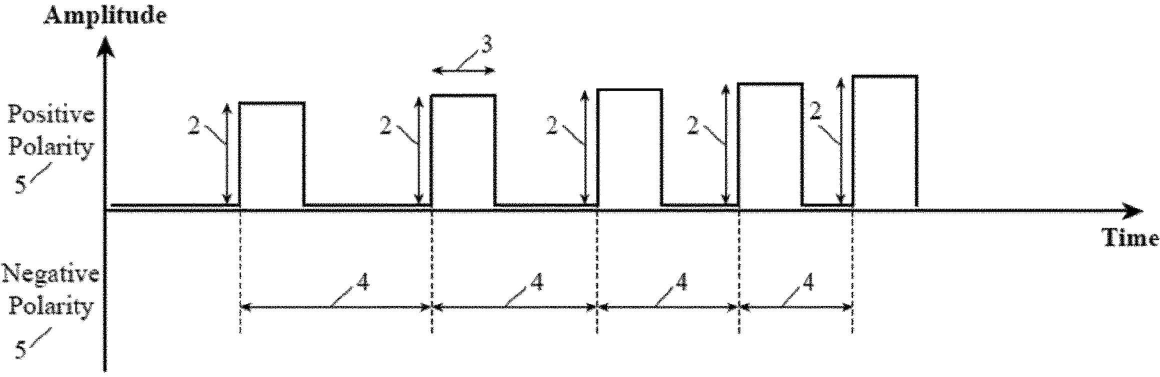
FIG. 28 depicts an exemplary stimulation pattern having ramping amplitude.

FIG. 28 shows a stimulation pattern where the impulse amplitude (2) increases at each impulse and where the impulse-to-impulse duration (4) increases at each impulse. The impulse polarity (5) and impulse duration (3) are constant for every impulse.

Example System

Figure 29:
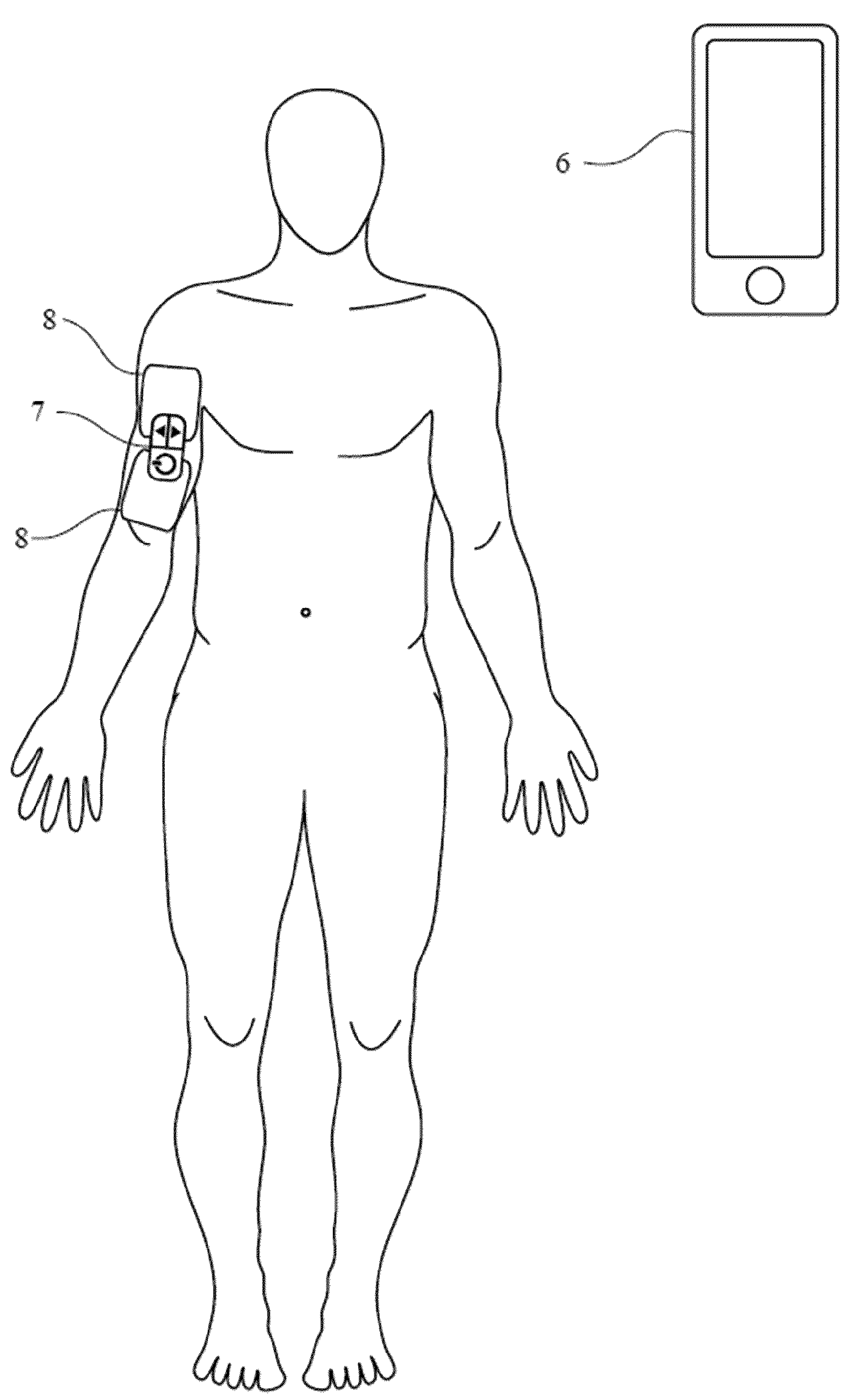
FIG. 29 depicts a system comprising a mobile device and a stimulation device according to an embodiment of the present invention.

FIG. 29 shows a possible embodiment of the invention where the stimulation pattern is first transferred wirelessly from a mobile device (6) to the stimulation device (7) with embedded motion sensing capability. The stimulation pattern or the impulse parameters can be adjusted in real time by the mobile device using the data provided by the motion sensor chip. The electrical stimulation is delivered to the user by the conductive media (8).

EMBODIMENTS

1. A method for encoding stimulation sequence pattern to deliver electrical stimulation to muscles and nerves comprising of:
2. The method of Embodiment 1 wherein the stimulation pattern consists of a header section containing the pattern metadata, a body section containing the impulse stimulation pattern and a footer section containing the error detection data.
3. The method of Embodiment 1 wherein the stimulation pattern is broken down into a set of different commands.
4. The method of Embodiment 1 wherein each command contains some or all impulse parameters and additional data allowing dynamic changes of one or multiple parameters.
5. The method of Embodiment 1 wherein the electrical impulses contained in a stimulation pattern are characterized by their amplitude, polarity, duration and impulse-to-impulse duration.
6. The method of Embodiment 1 wherein one or multiple impulse parameters are processed in a stimulation pattern command.
7. The method of Embodiment 1 wherein the stimulation pattern can be either predefined or calculated in real time using data provided by various sensors such as switches, biofeedback sensors or motion sensors.
8. A method for transferring the stimulation pattern to an electrical stimulation device pattern to deliver electrical stimulation to muscles and nerves comprising of:
9. The method of Embodiment 8 wherein the stimulation pattern is transferred wirelessly to the stimulation device.
10. The method of Embodiment 8 wherein the stimulation pattern is transferred by packets of data to the stimulation device.
11. The method of Embodiment 8 wherein the transfer protocol consists of three different steps: 1) initialization, 2) transfer and 3) verification.
12. The method of Embodiment 8 wherein the data transferred can contain the full stimulation pattern or just specific impulse parameters.

The invention claimed is:

1. A method for providing an encoded stimulation pattern to a device for providing electrical stimulation impulses to a user, the method comprising:

generating a header section, the header section comprising program metadata;

generating a body section, the body section comprising an impulse stimulation program;

generating a footer section, the footer section comprising error detection data;

concatenating the header section, body section, and footer section, to form an encoded stimulation pattern; and transmitting the encoded stimulation pattern to the device, wherein the encoded stimulation pattern is configured to affect a non-medical and/or non-therapeutic effect in the user.

2. The method according to claim 1, wherein the program metadata comprises at least one of: a pattern ID number; a pattern name; a number of phases; a maximal intensity; and a pattern duration.

3. The method according to claim 1, wherein the error detection data comprises a checksum.

4. The method according to claim 1, wherein the impulse stimulation program comprises an operational code and at least one parameter related to the operational code.

5. The method according to claim 4, wherein the operational code is selected from:

contraction; ramp; duration-frequency-modulation; duration-modulation; frequency-modulation; loop; back; phase; polarity; impulse-duration-multiply; and finish.

6. The method according to claim 4, wherein the at least one parameter is selected from: impulse frequency; impulse duration; number of impulses to generate; impulse start duration; impulse stop duration; relative address of array of impulse values; repeat program; end of array; repeat loop; phase number; intensity change percentage; phase duration; polarity value; and impulse duration multiply value.

7. A method for providing an encoded stimulation pattern to a device for providing electrical stimulation impulses to a user, the method comprising:

generating a header section, the header section comprising program metadata;

generating a body section, the body section comprising an impulse stimulation program;

generating a footer section, the footer section comprising error detection data;

concatenating the header section, body section, and footer section, to form an encoded stimulation pattern; and transmitting the encoded stimulation pattern to the device;

wherein the body section comprises a plurality of impulse stimulation programs.

8. A method for providing an adaptable encoded stimulation pattern to a device for providing electrical stimulation impulses to a user, the method comprising:

generating an encoded stimulation pattern;

transmitting the encoded stimulation pattern to the device;

receiving data from the device relating to a measured parameter of the user;

modifying the encoded stimulation pattern in response to the received data; and transmitting the modified stimulation pattern to the device;

wherein:

the encoded stimulation pattern comprises:

a header section, the header section comprising program metadata;

a body section, the body section comprising an impulse stimulation program; and a footer section, the footer section comprising error detection data; and the impulse stimulation program comprises an operational code and at least one parameter related to the operational code, and modifying the encoded stimulation pattern in response to the received data comprises at least one of:

changing the operational code; and increasing or decreasing at least one parameter.

9. The method according to claim 8, wherein the measured parameter of the user comprises at least one of: motion; heart rate; skin temperature; and skin bioimpedance.

10. The method according to claim 1, wherein the device for providing electrical stimulation impulses to a user is in communication with a mobile device, and wherein generating the encoded stimulation pattern and/or modifying the encoded stimulation pattern is performed on a processor on the mobile device.

11. The method according to claim 10, wherein the device for providing electrical stimulation impulses to a user communicates with the mobile device via a wireless communication protocol, optionally wherein the wireless communication protocol is Bluetooth Low Energy.

12. The method according to claim 1, wherein the encoded stimulation pattern and/or modified encoded stimulation pattern is transmitted to the device suitable to provide stimulation impulses to a user in multiple data packets.

13. A data processing apparatus comprising means for carrying out the steps of claim 1.

14. A computer program, comprising instructions which, when the pattern is executed by a computer, cause the computer program to carry out the steps of claim 1.

15. A computer readable storage medium having stored thereon the computer program of claim 14.

16. A device for providing electrical stimulation impulses to a user, comprising a data processing apparatus comprising means for carrying out the steps of claim 1, or a computer readable storage medium having stored thereon a computer program comprising instructions which, when the pattern is executed by a computer, cause the computer program to carry out the steps of claim 1.

17. A system, comprising:

a mobile device comprising: a data processing apparatus comprising means for carrying out a data processing apparatus comprising means for carrying out the steps of claim 1 and/or a computer readable storage medium having stored thereon a computer program comprising instructions which, when the pattern is executed by a computer, cause the computer program to carry out the steps of claim 1; and a device for providing stimulation impulses to a user, wherein the mobile device and the device for providing electrical stimulation impulses to a user are configured to communicate with one another via a wireless communication protocol.

* * * * *